United States Patent [19]

Morris et al.

[11] Patent Number: 6,017,738
[45] Date of Patent: *Jan. 25, 2000

[54] SOLID PHASE AMPLIFICATION PROCESS

[75] Inventors: Charles Phillip Morris, North Adelaide; Raymond John Harris, Adelaide, both of Australia

[73] Assignees: Adelaide Children's Hospital; University of South Australia, both of Adelaide, Australia

[*] Notice: This patent issued on a continued prosecution application filed under 37 CFR 1.53(d), and is subject to the twenty year patent term provisions of 35 U.S.C. 154(a)(2).

[21] Appl. No.: 08/761,862

[22] Filed: Dec. 9, 1996

Related U.S. Application Data

[63] Continuation of application No. 08/232,070, filed as application No. PCT/AU92/00587, Oct. 30, 1992.

[30] Foreign Application Priority Data

Nov. 1, 1991 [AU] Australia .................................. PK9224

[51] Int. Cl.[7] .................................. C12P 19/34; C12Q 1/68
[52] U.S. Cl. ........................ 435/91.2; 435/6; 435/91.1
[58] Field of Search ........................ 435/6, 91.1, 91.2, 435/810

[56] References Cited

U.S. PATENT DOCUMENTS

| | | | |
|---|---|---|---|
| 5,405,746 | 4/1995 | Uhlen | 435/6 |
| 5,629,158 | 5/1997 | Uhlen | 435/6 |

FOREIGN PATENT DOCUMENTS

| | | |
|---|---|---|
| 53294/86 | 8/1986 | Australia . |
| 14269/88 | 9/1988 | Australia . |
| 47144/89 | 6/1990 | Australia . |
| 63290/90 | 4/1991 | Australia . |
| 0370694 | 7/1991 | European Pat. Off. . |
| WO89/11546 | 11/1989 | WIPO . |
| WO90/06374 | 6/1990 | WIPO . |
| WO90/10716 | 9/1990 | WIPO . |
| WO90/11369 | 10/1990 | WIPO . |
| WO91/14788 | 10/1991 | WIPO . |

OTHER PUBLICATIONS

Proc. Natl. Acad. Sci. USA, vol. 86, pp. 2423–2427, Apr. 1989, Medical Sciences.

*Primary Examiner*—Kenneth R. Horlick
*Attorney, Agent, or Firm*—Evenson, McKeown, Edwards & Lenahan, P.L.L.C.

[57] ABSTRACT

A method for detecting a target nucleic acid sequence comprises: (a) providing a first primer hybridizing to the target nucleic acid sequence, wherein the primer is immobilized on an immobile solid phase support by a direct chemical linkage between the primer and the solid phase support, wherein the solid phase support forms a part of or is insertable into a container for a sample to be tested, (b) providing a second primer hybridizing to the target nucleic acid sequence in the opposite direction, wherein the second primer is labelled with a detectable label, (c) reacting the first and second primers with a sample containing nucleic acid sequences under conditions which allow amplification of the nucleic acid sequences that hybridize to the first and second primers in the container for the sample, and (d) detecting the presence of bound second primer. Alternatively, the label on the second primer can be attached or incorporated either during or after the amplification process. An assay system or kit for use in this method includes a first primer hybridizing to the target nucleic acid sequence, a second primer hybridizing to the target nucleic acid sequence in the opposite direction, and reagents for amplification of the sample containing nucleic acid sequences under conditions which allow amplification of the nucleic acid sequences that hybridize to the first and second primers in the container for the sample, and reagents for detection of the label on the bound second primer.

22 Claims, 6 Drawing Sheets

SDA (STRAND DISPLACEMENT AMPLIFICATION) (CONT)

HYBRIDIZE SDA PRIMERS TO DISPLACED STRANDS

FIG. 6

FINAL SPA-SDA PRODUCT

SOLID PHASE AMPLIFICATION PROCESS

This is a continuation application of Ser. No. 08/232,070, filed on Apr. 28, 1994, now abandoned, which was filed as PCT/AU92/00587 on Oct. 30, 1992.

BACKGROUND OF THE INVENTION

The present invention is generally in the field of methods for the detection of nucleic acid sequences through amplification and hybridization to labelled probes.

Hybridization methods are widely utilized in testing for the presence of particular nucleic acid sequences, identifying and/or quantifying such sequences. Hybridization occurs when there is sufficient complementarity of two nucleic acid sequences to effect non-covalent binding between the two molecules.

Various improvements and modifications have been introduced to increase the specificity and sensitivity of the reaction. In particular, polymerase chain reaction (PCR) techniques have been used to amplify the target nucleic acid sequence. In a recent development, two consecutive sets of PCR cycles ("nested PCR") have been used to both amplify and label the target nucleic acid sequence. The labelled sequence is then immobilized on a solid phase carrier, and testing is carried out using a reagent specific to the label. (See D J Kemp, et al., "Colorimetric detection of specific DNA segments amplified by polymerase chain reactions", *Proc. Natl. Acad. Sci. USA* 86, pp. 2423–2427, 1989).

WO89/11546 by Paulsen, et al., describes a method using PCR with DNA primers, one of which is soluble and the other which is bound to superparamagnetic particles, allowing greater ease of separation of the amplified product which facilitates detection. While the nucleic acid is bound to the particle, however, amplification via the beads is still taking place in a soluble phase, ie the beads are suspended in a liquid phase, increasing the time and complexity of the reaction, and requiring equipment for isolation of the superparamagnetic particles.

AU A-47144/89 by Molecular Diagnostics, Inc. also reports a method for increasing detection of nucleic acids using PCR to amplify sequences, where one or both of the primers are in solution or immobilized or immobilizable, for example, to Sephadex, to facilitate detection. The process can be used to yield immobilized target nucleic acid.

However, prior art methods for amplifying nucleic acid sequences have all suffered from problems associated with carrying out reactions in the liquid, rather than solid, phase. After each step of the reaction, the intermediate product must be isolated, before being reacted in the next step. Isolation steps are cumbersome, time consuming and often involve labile linkage reagents. In addition, no isolation step can be completely successful.

It is therefore an object of the present invention to provide a method which is rapid, simple, and provides an accurate, sensitive means for detecting small amounts of nucleic acid in a test sample.

It is a further object of the present invention to provide an assay which is relatively inexpensive, simple, rapid, and provides an accurate, sensitive means for detecting small amounts of nucleic acid in a test sample in clinical and research laboratories.

SUMMARY OF THE INVENTION

The present invention utilizes the concept of amplification of a target nucleic acid by means of two primers, one of which is directly immobilized onto a sample container surface, and the other which is labelled for ease of detection. By definition, both primers must be hybridizable with a target nucleic acid sequence. According to the method for determining the presence of a target nucleic acid sequence in a sample, the sample is placed in a container with the immobilized nucleic acid primer. The target sequence is then amplified using a second labelled primer or labelled polymerase substrate which, on incorporation, allows detection and quantification via the label on the solid phase amplified nucleic acid sequence.

Examples demonstrate the detection of the gene for cystic fibrosis and a specific type of mycoplasma in patient samples.

DETAILED DESCRIPTION OF THE INVENTION

The assay and method of use described herein have the following elements: a target molecule to be detected in any test or patient sample, a first primer which is immobilized to a solid surface suitable for containment of the patient sample and is hybridizable to the target molecule, a second primer which can be detected using a variety of different methodologies and is hybridizable to the target molecule, and means for amplification of the target sequence via the two primers.

A common problem in laboratories utilizing diagnostic methods based on nucleic acid amplification is the occurrence of false positives. This problem invariably arises due to the contamination of the laboratory with amplified target molecules (amplicons). Of relevance here is the intrinsic high level of amplicon containment offered by solid phase amplification (SPA). SPA requires very little manipulation of solution phase amplicons. Such amplicons are removed from SPA reactions by simple washes and can be readily destroyed. Additionally, the solid phase amplicons offer little or no contamination threat. This level of containment is unmatched by any other amplification process. Thus SPA offers a high degree of amplicon containment.

The Target Molecule

This method allows detection and identification of virtually any nucleic acid sequence, and thus allows the detection and identification of viruses, microorganisms and parasites, the detection of genetic diseases, either by detection of sequence variations (mutations) which cause or are associated with a disease or are linked (Restriction Fragment Length Polymorphisms or RFLP's) to the disease locus, and sequence variations which are associated with, or cause, cancer, and the detection and identification of nucleic acid sequences for forensic fingerprinting, tissue typing and for taxonomic purposes, namely the identification and speciation of microorganisms, flora and fauna, and for the production of solid phase nucleic acid templates for DNA and RNA sequencing. The methodology is also useful for other applications.

The following are a few examples of such applications:

1. Pathogen Detection
   Detection of viruses (HIV, hepatitis viruses, papilloma).
   Detection of microorganisms (Mycobacteria, Legionella, Mycoplasmas).
   (Applications in clinical medicine, veterinary science, aquaculture, horticulture and agriculture).
2. (a) Detection of sequence variations which cause or are associated with a disease or are genetically linked to a disease locus. Examples cover genetic diseases and cancer.
   e.g. Point mutations—sickle cell anaemia, phenylketonuria, Lesch Nyhan syndrome.
   Small deletions—Cystic fibrosis (ΔF508).
   Large deletions—thalassaemias, Duchenne muscular dystrophy.
   Sequence reiteration—Fragile X.
   RFLP's (Restriction Fragment Length Polymorphisms)—Huntington's chorea, thalassaemias, cystic fibrosis.
   (b) Population screening for carriers of serious genetic diseases, where the incidence of carriers is high and the number of mutations is low, e.g., cystic fibrosis, and Tay Sach's disease in Ashkenazi Jews.
3. Cancer—detection of predisposing sequences, e.g., Philadelphia chromosomes in chronic myelogenous leukemia, antibody gene rearrangements, specific deletions; detection and monitoring of treatment, remission and relapse.
4. Tissue typing—determination of HLA genotypes.
5. Forensic applications—e.g., VNTR DNA fingerprinting of individuals and obtaining DNA fingerprints from forensic samples.
6. Maternity and paternity testing.
7. Foetal sex determination
8. Taxonomy—Classification and speciation of organisms.
9. Quality control in agriculture and the food and pharmaceutical industries, e.g., assessment of authenticity of food products.

The assay and method of use described herein are equally applicable to RNA (ribonucleic acid) sequences, as well as DNA (deoxyribonucleic acid) sequences, although it may be necessary to produce a cDNA copy of RNA sequences.

Primers

The primers are synthesized to be complementary to the target molecule. In general these are approximately 15 to 30 nucleotides in length and flank a portion of the target molecule. One hybridizes to the 5' end of a portion of the target molecule, the other to the 3' end of a portion of the target molecule. All appropriate reagents and equipment are commercially available.

Solid Phase Support

One primer is attached using known methodology, as described below, to a solid phase support. The advantages of the system described herein is that the solid support forms or is readily insertable into the container for the patient sample, eliminating the need for separate centrifugation, magnetic collection, filtration or other separation steps, as required by the prior art methods, for example, to separate superparamagnetic beads. A preferred material is the microtiter well plates that are commercially available.

The solid support may be any structure having a surface which can be derivatised with a nucleic acid primer, such that the primer can participate in solid phase nucleic acid amplification. In the preferred embodiment, the solid support is an immobile solid phase material, for example, the side of a microtiter well or a dip stick.

Specific preferred supports include:

1. The inside surface of wells of any microtitre trays, e.g., Covalink trays—Nunc.
2. Microtitre tray lids with protrusions which fit into microtitre trays, e.g. Fast Elisa dish—Falcon.
3. Dipsticks for low volume applications, e.g., suburban and country medical practices.

These all offer the potential for high volume diagnostic applications for solid phase amplification (SPA), especially if isothermal (single temperature) amplification is used.

It is surprising that solid phase amplification of nucleic acids on the surface of a microtiter well produces a significant amount of amplified product due to the inherently less favourable kinetics of solid phase molecular interactions, versus those of the solution phase. The results demonstrate that, despite the slightly slower rate of amplification using a solid phase as compared with solution phase, or with bead-based amplification, which offers a vary large surface area, the system offers a rapid, sensitive, and clinically viable method of nucleic acid amplification.

Although described herein as preferentially involving binding of the first primer to the solid phase before initiation of amplification, in some cases it may be desirable to combine conventional liquid phase amplification techniques with the solid phase amplification (SPA) procedures. For instance, if the target nucleic acid molecule is only likely to be present in very small quantities, then it maybe beneficial to carry out an initial liquid phase amplification in the vessel to which the primer is bonded. This liquid phase amplification step may involve a small proportion of the first primer or it may involve other primers. When the target molecule is amplified to a sufficient level, then the SPA process takes over.

Anchoring of the First Primer to Solid Phase Support

Any method for linking nucleic acid sequences to solid supports may be used. For example, any of the following methods are suitable:

1. Amide linkage of primer to a solid phase

| Secondary amine on the wall of a CovaLink plate | activated spacer arm - suberic acid bis (N-hydroxy-succinimide) | synthetic oligodeoxy-nucleotide (eg. 20 nucleotides long and containing an added primary amino group) |

Derivatisation sequence:

(1) The surface bound (solid phase) secondary amine (on walls of wells of CovaLink plates) is reacted with the activated spacer arm.

(2) The solid phase activated spacer arm is reacted with the primary amino group of the synthetic oligodeoxynucleotide, to form the product, which is a solid phase primer (amide linkage), as shown below.

amide linkage

2. Amidate linkage of primer to a solid chase (a) A 5'-phosphorylated oligodeoxynucleotide (e.g. 20 nucleotides long) is reacted with a phosphate activating compound, preferably a water-soluble carbodiimide such as EDC (1-ethyl-3-(3-dimethylaminopropyl)-carbodiimide).

phosphoramidate linkage

Product - solid phase primer (phosphoramidate linkage)

3. Thioether linkage of primer to a solid chase

The reaction sequence is as follows:

(1) Bromoacetic acid—NHS is reacted with the secondary amino group on the solid support.

(2) The thiol group of the oligodeoxynucleotide is reacted with the bromomethyl group of the intermediate product formed in step (1).

| Secondary amine on wall of well of CovaLink tray | NHS activated bromoacetic acid | oligodeoxynucleotide with 5'-thiol group | thioether linkage

Product solid phase primer (thioether linkage).

Product solid phase primer (thioether linkage).

4. Introduction of amino groups onto the surface of microtitre tray wells

Plates were nitrated with acetyl nitrate using the method of R. Taylor, "Electrophilic aromatic substitution" p. 269 (J. Wiley and Sons 1990). Reduction was via $SnCl_2$.

Amplification Procedures

Currently known methods of nucleic acid amplification include:

(a) PCR (Polymerase Chain Reaction).

(b) LCR (Ligation Chain Reaction).

(c) NASBA (Nucleic Acid Sequence Based Amplification), using RT/RNAse H/$T_7$ polymerase.
RT=reverse transcriptase.
RNAse H=ribonuclease H
$T_7$ polymerase =$T_7$ bacteriophage RNA polymerase.

(d) Qβ replicase based amplification.

(e) Strand displacement amplification (SDA).

The principles of some of these amplification methods are described below.

PCR (Polymerase Chain Reaction)

Figure 1:
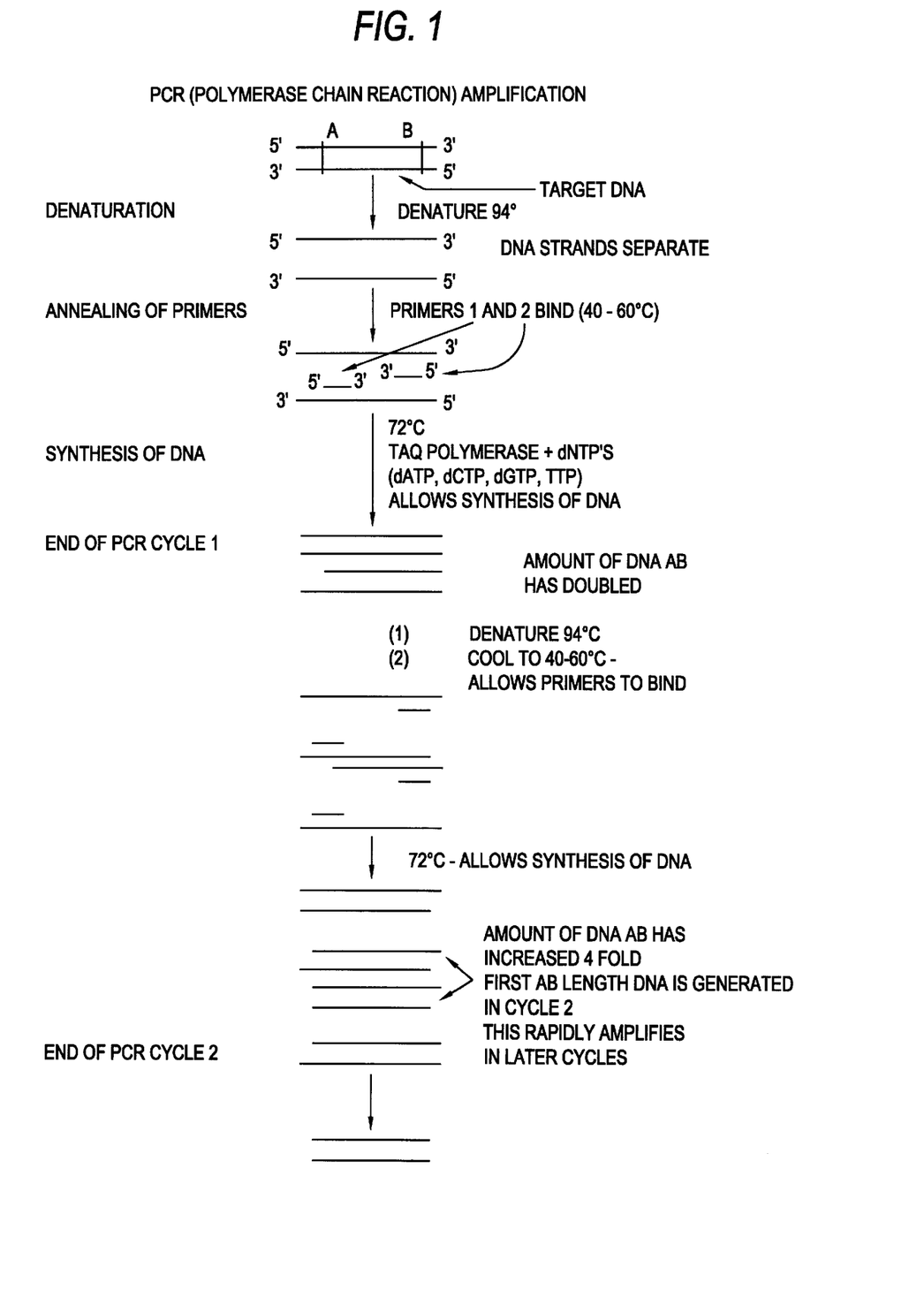
FIG. 1 is a schematic of the PCR (Polymerase Chain Reaction).

Polymerase chain reaction procedures and reagents are commercially available and described in the literature, for example, by R. K. Saiki, et al., "Enzymatic Amplification of β-globin Genomic Sequences and Restriction Site Analysis for Diagnosis of Sickle Cell Anemia", *Science* 230, pp. 1350–1354, 1985. Refer to FIG. 1.

LCR (Ligation Chain Reaction)

Figure 2:
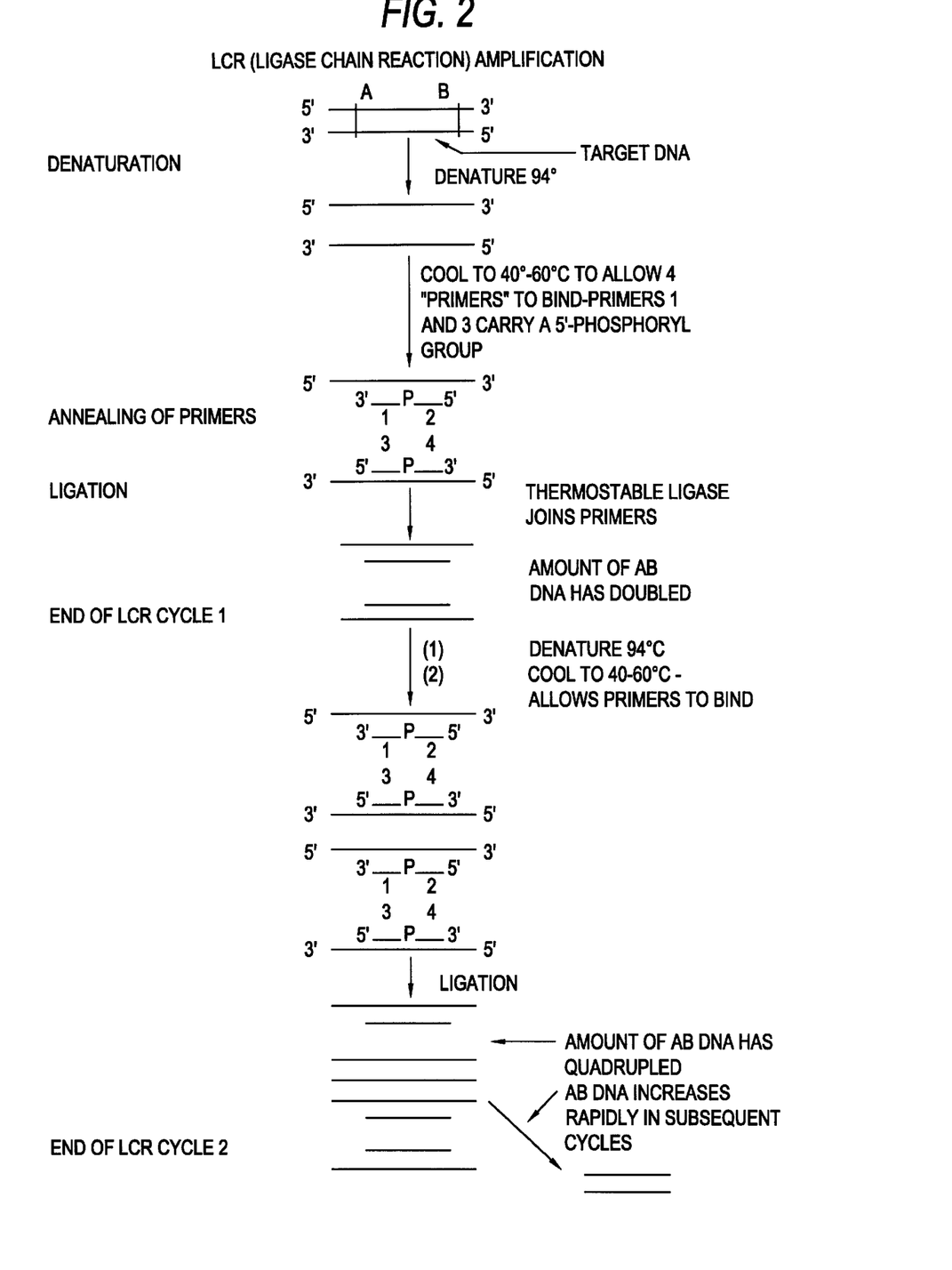
FIG. 2 is a schematic of the LCR (Ligase Chain Rection).

The ligation chain reaction is well known and described in the literature, for example, by U. Landegren, et al., "A Ligase-mediated Gene Detection Technique", *Science* 241, pp. 1077–1080, 1988. Refer to FIG. 2.

NASBA (Nucleic Acid Sequence Based Amplification)

This method is also well established in the literature, as described, for example, by J. Cuatelli, et al., "Isothermal in Vitro Amplification of Nucleic Acids by a Multienzyme Reaction Modelled After Retroviral Replication", *Proc. Natl. Acad. Sci. USA* 87, pp. 1874–1878, 1990.

Figure 3:
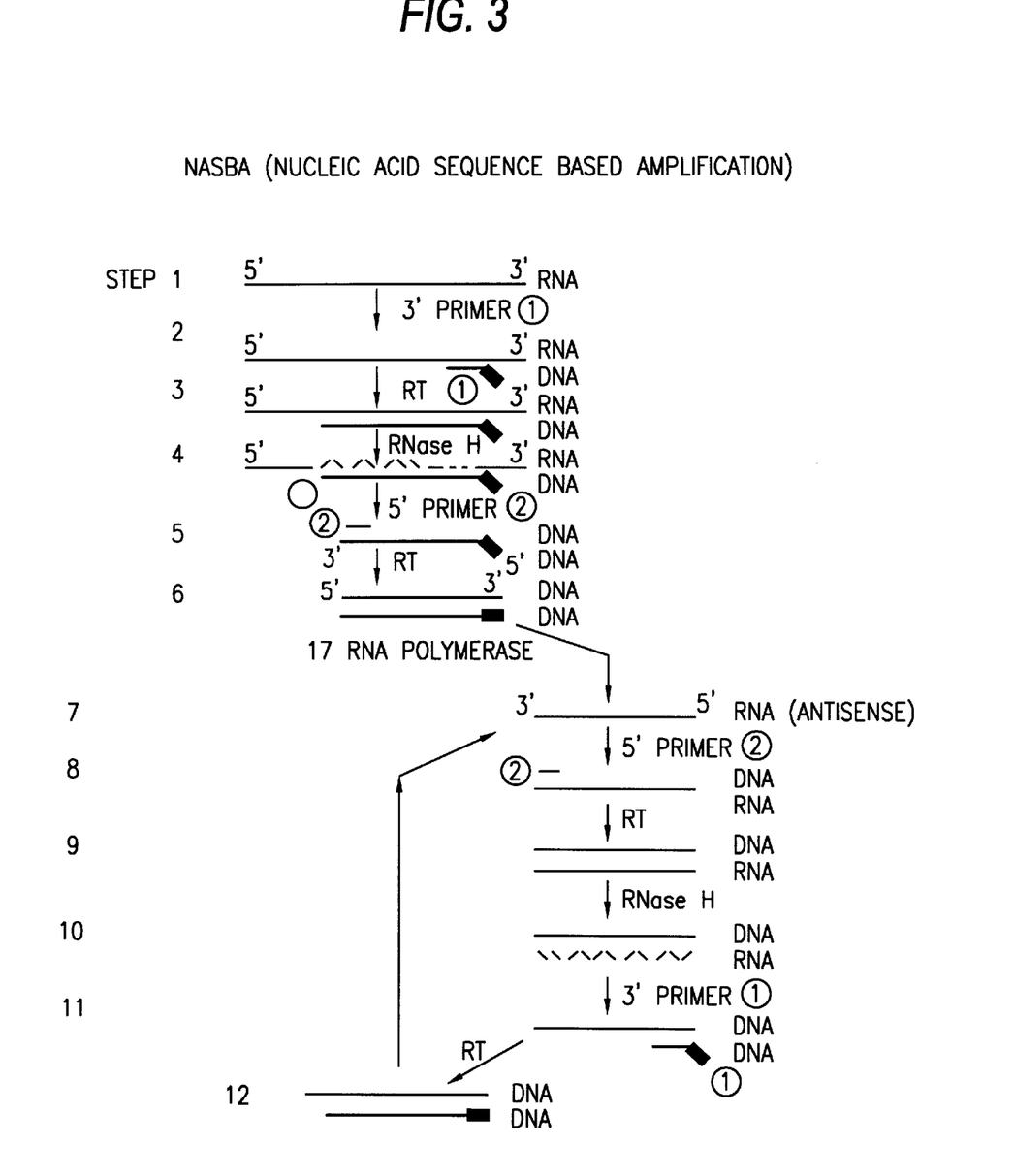
FIG. 3 is a schematic of the NASBA (Nucleic Acid Sequence Based Amplification). Thin lines, RNA; thick lines, DNA; RT, reverse transcriptase.

The strategy of the NASBA scheme is shown in FIG. 3. The reaction depends on a continuous cycle of reverse transcription and transcription reactions to replicate an RNA target by means of cDNA intermediates. DNA targets can also be amplified. Primers 1 and 2 prime DNA synthesis and Primer 1 encodes the promoter sequence for the T7 RNA polymerase (black boxes). Steps 1–6 depict the synthesis of a double-stranded cDNA, which is a transcription template for T7 RNA polymerase. Complete cDNA synthesis is dependent on the digestion of the RNA in the intermediate RNA-DNA hybrid (step 4) by RNase H. Transcription-competent cDNAs yield antisense RNA copies of the original target (step 7). These transcripts are converted to cDNAs containing double-stranded promoter on one end (steps 7–12).

These cDNAs yield antisense RNAs, which can re-enter the cycle.

CHARACTERISTICS OF NUCLEIC AMPLIFICATION SYSTEMS excess, bind the target strands at positions flanking the sequence to be amplified. Primers $S_1$ and $S_2$ have HincII recognition sequences (5' GTTGAC) located 5' to the target complementary sequences. The four primers are simultaneously extended by exo-klenow using dGTP, dCTP, TTP and dATPS. Extension of BE displaces the $S_1$ primer extension products, $S_1$-ext. Likewise, extension of $B_2$ displaces $S_2$-ext. $B_2$ and $S_2$ bind to displaced $S_1$-ext. Bi and $S_1$ bind to displaced $S_2$-ext. Extension and displacement reactions on templates $S_1$-ext and $S_2$-ext produce two fragments with a hemiphosphorothiote HincII at each end and two longer fragments with a hemiphosphorothioate HincII site at just one end. HincII nicking and exo-klenow extension/displacement reactions initiate at these four fragments, automatically entering the SDA reaction cycle depicted in FIG. 5b. Sense and antisense DNA strands are differentiated by thin and thick lines. HincII recognition sequences are depicted by (thin line-thick line-thin line).

Figure 5A:
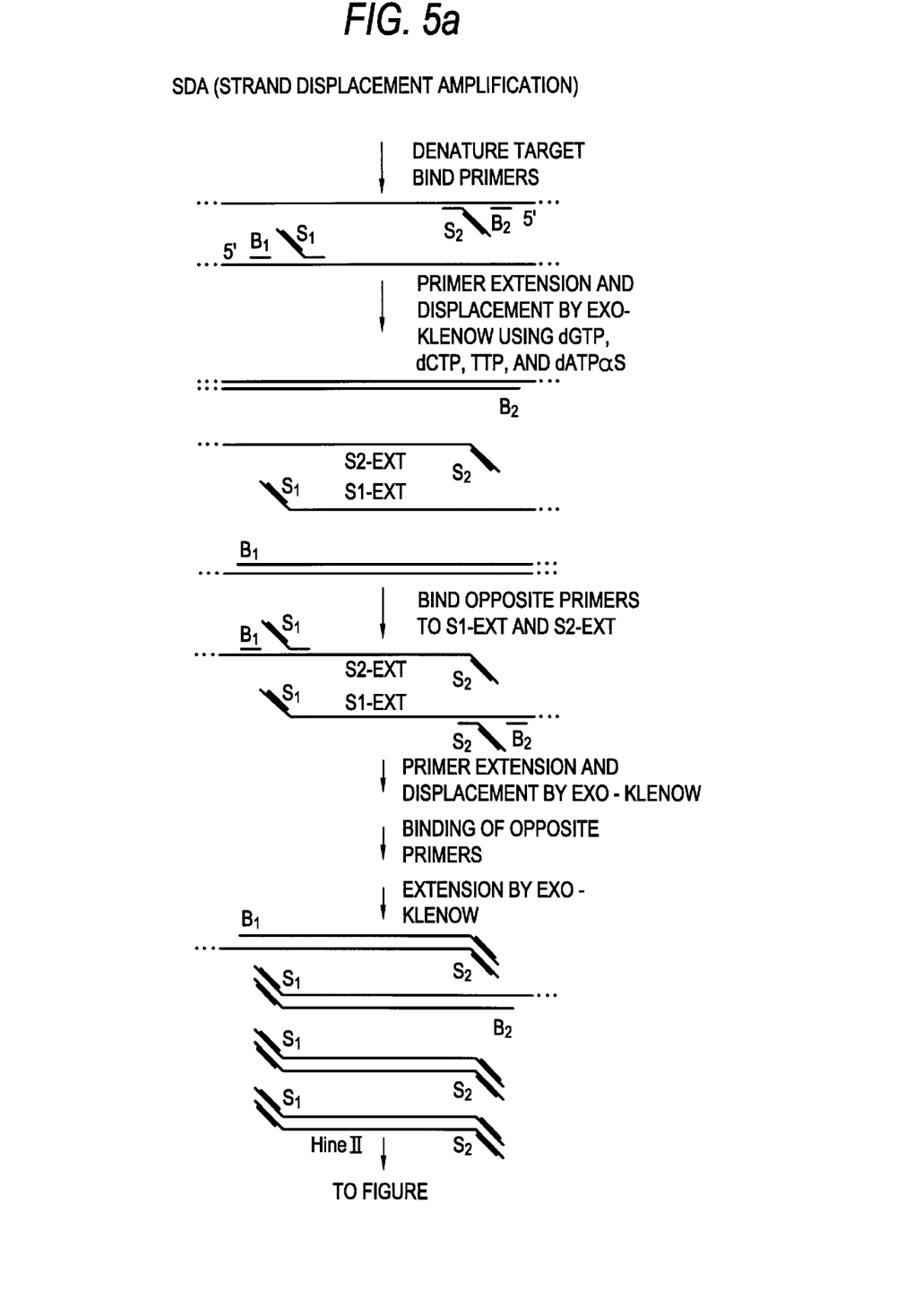
FIG. 5a is a schematic of the target generation scheme for SDA (Strand Displacement Amplification).
Figure 5B:
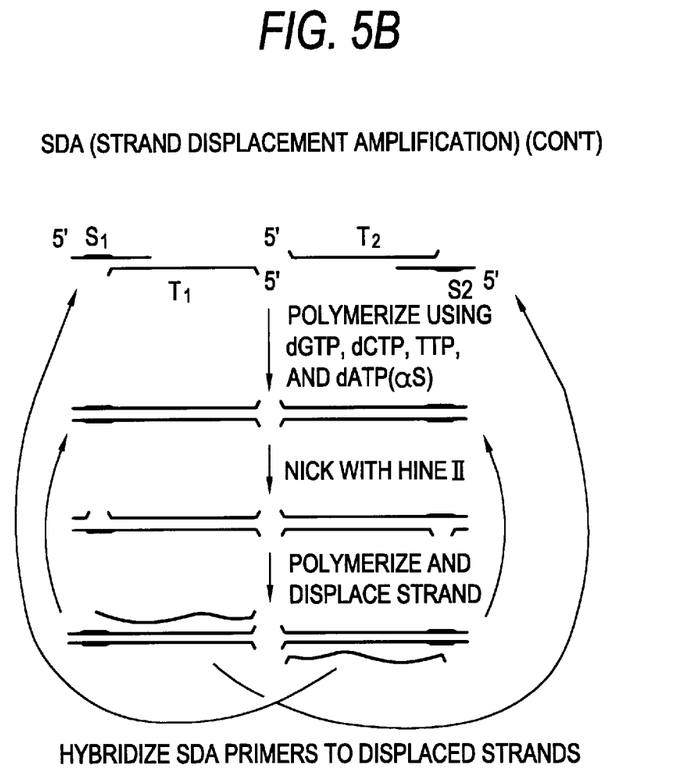
FIG. 5b is a schematic of automatically entering the SDA reaction cycle.

The SDA reaction cycle is shown in FIG. 5b. These reaction steps continuously cycle during the course of amplification. Present in excess are two SDA primers ($S_1$ and $S_2$). The 3'-end of $S_1$ binds to the 3'-end of the displaced target strand $T_1$, forming a duplex with 5'-overhangs. Likewise, $S_2$ binds $T_2$. The 5'-overhangs of $S_1$ and $S_2$ contain the HincII recognition sequence (5' GTTGAC). Exo-klenow extends the 3'-ends of the duplexes using dGTP, dCTP, TTP and dATPS, which produces hemiphosphorothiote recognition sites on $S_1$.TL and $S_2.T_2$. HincII nicks the unmodified primer strands of the hemiphosphorothiote recognition sites, leaving intact the modified complementary strands. Exo-klenow extends the 3'-end at the nick on $S_1$.TL and displaces the

|   | One primer incorp-orated | Two or more primers incorp-orated | Double-stranded product | Can be labelled at non-anchored end | Can be internally labelled | Requires temperature cycling |
|---|---|---|---|---|---|---|
| 1. PCR | + | + | + | + | + | + |
| 2. LCR | + | + | + | + | + | + |
| 3. NASBA RT/T7 | + | + | + | + | + | No 42•only* |
| 4. QB |   |   |   |   | + | No |
| 5. SDA | + | + | + | + | + | No |

*Big technical advantage.

Figure 4:
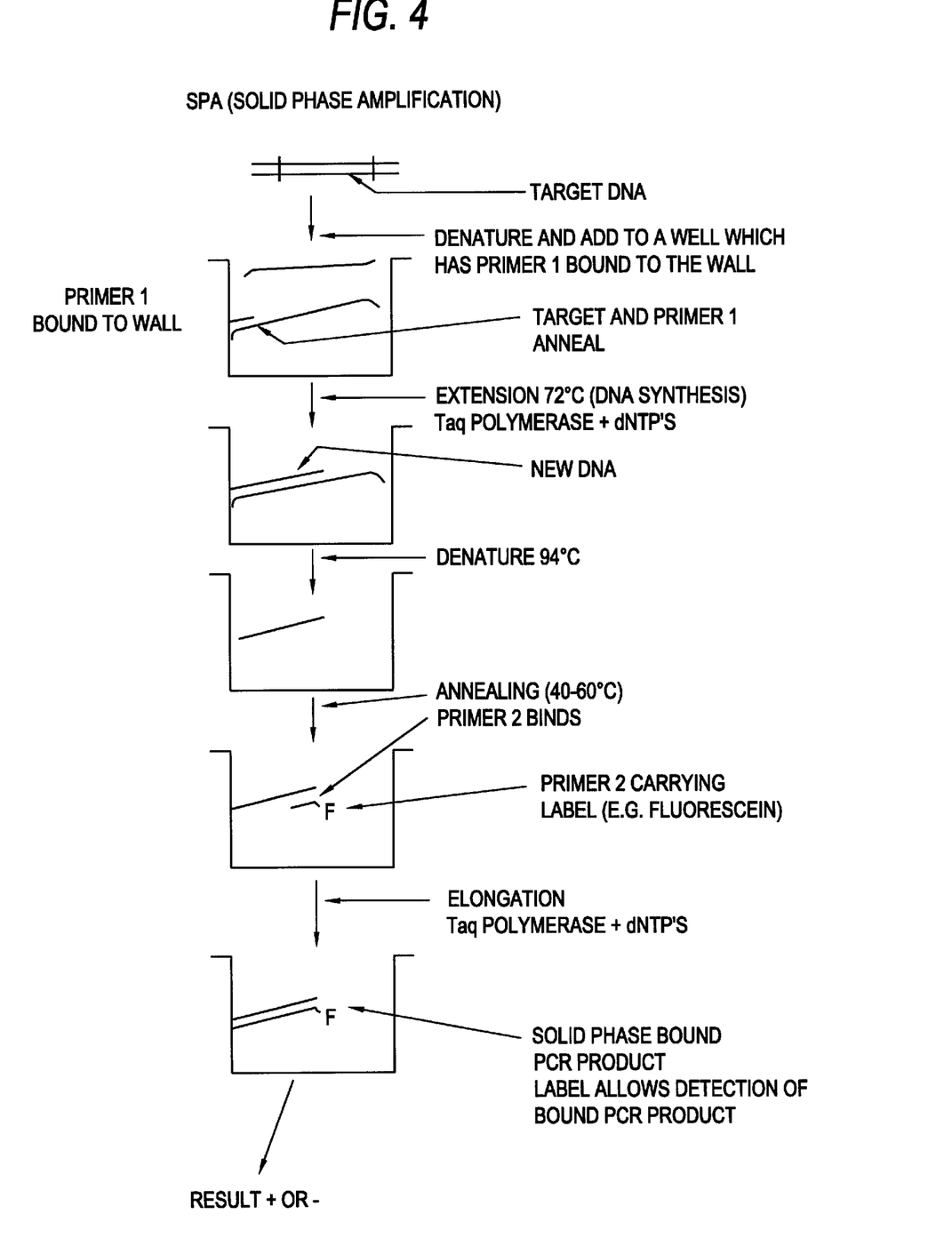
FIG. 4 is a schematic of the SPA method for amplification.

The process of solid phase amplification (SPA) of a target nucleic acid sequence, using PCR as the method for amplification, is illustrated in FIG. 4.

One primer is immobilized to the wall of the plate, and the other is labelled with a fluorescent label. As shown by this diagram, generally 20–30 cycles are needed to amplify sufficient DNA for detection. The plate is then washed to remove unincorporated primer 2 and the plate read using a plate fluorimeter. A positive result indicates the presence of the target nucleic acid, a negative result indicates that the target nucleic acid is not present.

SDA (Strand Displacement Amplification)

The following scheme is taken directly from G. T. Walker, et al., "Strand displacement amplification—an isothermal, in vitro DNA amplification technique", *Nuc. Acid Res.* 20, pp. 1691–1696, 1992.

The target generation scheme for SDA is shown in FIG. 5a. This figure depicts the initial steps in an SDA reaction which transform the original target sequence into the amplification cycle depicted in FIG. 5b. A target DNA is heat denatured. Four primers ($B_1$, $B_2$, $S_1$ and $S_2$), present in downstream strand that is equivalent to $T_2$. Likewise, extension at the nick on $S_2.T_2$ results in displacement of $T_1$. Nicking and polymerization/displacement steps cycle continuously on $S_1.T_1$ and $S_2.T_2$ because extension at a nick regenerates a nickable HincII recognition site. Target amplification is exponential because the strands displaced from $S_1T_1$ serve as target for $S_2$ while strands displaced from $S_2.T_2$ serve as target for $S_1$. Sense and antisense DNA strands are differentiated by thin and thick lines. Intact and nicked HincII recognition sequences are depicted by (thin line-thick line-thin line) and (thin line-thick line, space, thick line-thin line), respectively. The partial HincII recognition sequence 5' GAC and its complement 5' GTC are present at the 5'-and 3'-ends of displaced strands as represented by (thick line-thin line) and (thin line-thick line).

The following modifications of SDA (see Walker et al., 1992 *Nuc. Acid Res* 20, 1691–1696) are required to allow implementation of SPA.

These modifications should be read in conjunction with FIG. 5.

1A Primers $S_1$ and $S_2$ are chemically prepared to contain HincII recognition sequences which are resistant to cutting by this enzyme, i.e., primers $S_1$ and $S_2$ are chemically prepared to contain phosphorothioate nucleotides using known methodology.

1B Primer S2 carries a detector tag, introduced during chemical synthesis, for example, a 5'-biotin group or 5'-fluorophore.

2 Only standard dNTPs are then required for amplification (i.e., dATPS are not be used).

With regard to the SPA version of SDA the process proceeds as follows:

(a) Primer S1 is covalently bound via the 5'-end to the microtitre well surface.

(b) Biotinylated primer S2 is free in solution.

Figure 6:
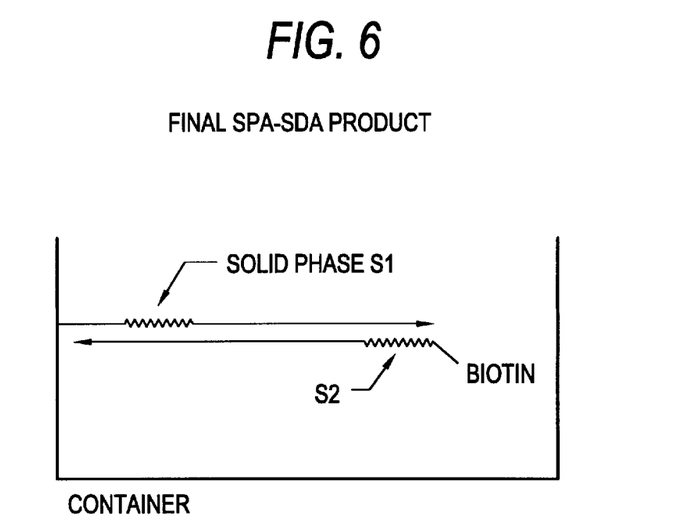
FIG. 6 is a schematic of the reaction products of the modified SDA process.

(c) SPA-SDA isothermal amplification is followed by a simple wash to yield a final solid phase double stranded product as shown in FIG. 6.

(d) The label is then used to detect the bound target molecule. For example biotin would then be detected colorimetrically via avidin-horseradish peroxidase or fluorimetrically via avidin-Europium.

It is also possible to improve the amount of solid phase product produced by the inclusion of a small quantity of primer S1 in the solution phase to increase the quantity of the target in solution.

(b) Biotin label (i) Biotinylated primer 2.

(ii) Biotinylated dNTPs, e.g. biotinylated dATP.

SPA product: Biotin labelled anchored nucleic acid.

Detection systems:

(i) Europium labelled avidin, with quantification of Europium by time resolved fluorescence spectroscopy.

(ii) Avidin—horseradish peroxidase, with quantification of the resulting coloured product by spectroscopy (e.g., plate reader).

(iii) Avidin—alkaline phosphatase, with quantification of the resulting coloured or fluorescent product by standard or fluorescent spectroscopy.

Other labels include radiolabels, other enzyme systems, and dyes, as well as nucleotides with altered emission spectra.

The present invention is further demonstrated by reference to the following non-limiting examples.

EXAMPLE 1

Affigel Anchored Solid Phase Amplification (SPA)

Product:
Primer 1 bound to Affigel™ beads (amide linkage).

Detection Labels

Any suitable method for labelling nucleic acid sequences can be used, e.g., fluorescent labelling, biotin labelling or enzyme labelling. The label is introduced into the anchored amplified nucleic acid product either via labelled primer 2 or via labelled nucleotide substrates.

Exemplary detection systems include:

(a) Fluorescent labelling and detection

Source of fluorescent label:

(i) Fluorescent primer 2, e.g., fluorescein-primer 2.

(ii) Fluorescent derivatives of ribo or deoxyribo-NTPs (substrates for RNA and DNA polymerases, respectively).

SPA Product: fluorescently labelled anchored nucleic acid.

Detection system: fluorescent plate reader or other fluorescence detection system.

The DNA sequence to be amplified was a portion of the CFTR (cystic fibrosis transmembrane conductance regulator) gene.

Amplification was by the polymerase chain reaction (PCR).

The PCR conditions were as follows:

10 mM Tris-HCl (pH 8.3 at 25° C.), 2.5 mM $MgCl_2$, 50 mM KCl, 0.1% v/v Triton x 100, 0.04% w/v gelatin, 0.4 mM dNTP's, Primer 2 250 ng, normal human DNA, 0.5 µg (note: dried blood spot on paper diameter 3.0 mm was used for some reactions). Taq polymerase 2.5 units. Cycling conditions: 30 sec 94° C., 60 sec 729° C., 30 sec 55° C., 30 cycles.

In this particular embodiment, the SPA product was labelled with biotin, rather than a fluorescent label.

Detection of SPA Product

The Affigel™ bound product was detected by use of Europium labelled avidin and time resolved fluorescence spectroscopy. The results are shown in Table 1.

TABLE 1

Results of CFTR gene Test.

| Affigel-primer 1 (µl) | Target | Test Counts | Denatured[a] Control Counts | Test counts Control Counts |
|---|---|---|---|---|
| 1 | 0.5 µg DNA | 35,000 | 6,400 | 5.5 |
| 2 | 0.5 µg DNA | 74,000 | 3,800 | 20 |
| 5 | 0.5 µg DNA | 550,000 | 22,000 | 25 |
| 10 | 0.5 µg DNA | 1,300,000 | 110,000 | 12 |
| 20 | 0.5 µg DNA | 1,400,000 | 150,000 | 9 |
| 10 | 3 mm blood disc | 60,000 | 6,000 | 10 |
| 20 | 3 mm blood disc | 42,000 | 4,800 | 8.8 |
| 10 | boiled extract of 3 mm blood disc | 112,000 | 8,000 | 14 |
| 20 | boiled extract of 3 mm blood disc | 180,000 | 12,000 | 15 |
| Control 10 | No DNA | 54,000 | 12,000 | 4.6 |
| Control 20 | No DNA | 83,000 | 34,000 | 2.5 |

[a]The SPA product can be treated at pH 9.8 to dissociate the biotin labelled DNA strand from the primer anchored DNA strand.

Conclusion:

5–10 µl of Affigel™-primer 1 is an efficient solid support for SPA for either purified DNA or DNA of 3 mm blood discs.

EXAMPLE 2

SPA Detection of the CFΔPhe 508 Mutation

The amplification reagents and conditions were as follows:

Primers:

Common primer carrying 5'-biotinyl group 5'-biotin-GTT GGC ATG CTT TGA TGA CGC TTC-3'.

Primer for detection of Δ F 508 mutation Δ F 508 5'-(T)$_{10}$ GGC ACC ATT AAA GAA AAT ATC ATT GG-3'.

Normal primer for detection of normal sequence 5'-phosphate-TTT TTT TTT GGA TCC GGC ACC ATT AAA GAA AAT ATC ATC TT-3'.

Each SPA 50 µl reaction contained ~67 mM Tris HCl pH 8.8 at 25° C., 16.6 mM ammonium sulphate, 0.45% Triton X-100, 200 µg/ml gelatin, 200 µM each of dATP, dCTP, dGTP, TTP, 3.0 mM MgCl$_2$, 250 ng of 51 biotin primer, 2.5 units Taq polymerase.

SPA was performed in Costar microtitre wells previously nitrated with acetic anhydride/nitric acid and reduced by tin chloride to give wells which carried amino groups covalently attached to the well walls.

The normal or ΔF 508 primers were covalently linked to amino groups on the well walls via the amidate linkage method. Product detection was via avidin-Europium and time resolved fluorescence quantification and colorimetrically by avidin-horseradish peroxidase.

SPA cycle amplification conditions 1 min 95° C.
1 min 57° C.
1 min 72° C.

Initial denaturation for 7 minutes at 95° C. and final extension for 10 minutes at 72° C.

TABLE 2

Results of SPA ΔF 508 Mutation screen.

| Template | TRF Counts | Absorbance at 450 nm |
|---|---|---|
| Wild type 500 bp PCR product | 1,000,000 | 1.8 |
| ΔF 508 500 bp PCR product | 10,000 | 0.2 |
| Wild type genomic DNA | 45,000 | 0.8 |
| ΔF 508 genomic DNA | 10,000 | 0.15 |
| Salmon sperm DNA (sonicated) | 10,000 | 0.15 |
| No template | 10,000 | 0.2 |

Table 2 shows signals obtained with the wild type primer immobilized on the wells, following solid phase amplification of different templates. Additionally the signal with genomic DNA was increased to approximately 400,000 counts when 45 cycles were used. Additionally, when some of the solid phase primer was added in solution the signal was greatly increased from genomic DNA as a target.

For example, detection of the normal Cystic Fibrosis gene, addition of normal primer to the solution gave the following results:

2 ng normal primer in solution gave a product signal of 80,000 counts 5 ng normal primer in solution gave a product signal of 1,000,000 counts 10 ng normal primer in solution gave a product signal of 1,200,000 counts 20 ng normal primer in solution gave a product signal of 1,200,000 counts When the mutant ΔF 508 primer was immobilized signals obtained were similar to those in the table when ΔF 508 DNA was used as a template.

EXAMPLE 3

Detection of *Mycoplasma pneumoniae*—the Major Causative Agent of Atypical Pneumonia Primers Solution phase primer 5'-biotinyl-TCA AAA CAA CGA CAC3' corresponds to nucleotides 3863–3877 of the P1 gene.

Solid phase primer 5'-TTT CAG AAA GTC GAC-3' corresponds to nucleotides 4114–4100 of the P1 gene, 5'-phosphorylated with polynucleotide kinase and ATP.

Preparation of DNA from *M. Pneumoniae*

Various amounts (in colony forming units—CFU) of whole *M. pneumoniae* cells were added to normal nasopharyngeal aspirate and were collected by centrifugation and the pellet was treated with proteinase K (30 µl, 200 µg/ml proteinase K, 10 mM Tris-HCl pH 8.3) at 37° C. for 1 hour to liberate the DNA, then at 95° C. to inactivate the proteinase K.

SDA reaction mix as for cystic fibrosis ΔF 508 detection except primers were as given above.

Microtitre Plates

Plates derivatized with solid phase primer were prepared as for the cystic fibrosis ΔF 508 detection system.

Amplification Conditions 30 cycles of amplification using

90° C. for 1 min
40° C. for 1 min
60° C. for 3 min

The initial denaturation was 7 min at 95° C. and the final extension was 10 min at 72°C.

TABLE 3

Product detection was via Avidin-Europium and time resolved fluorescence quantification of Europium

| M. Pneumoniae CFU | Counts |
|---|---|
| $10^7$ | 593,000 |
| $10^6$ | 263,000 |
| $10^5$ | 280,000 |
| — | 48,000 |

The following organisms did not give a positive signal (signals 14,000–47,000): *M. buccale, M. fermentans, M. genitalium, M. hominis, M. hyorrhinis, M. salivarium, A. laidlawii A, A. laidlawii B*.

Additionally five patients with confirmed M. pneumoniae infection with greater than $10^5$ CFU/ml of respiratory secretion gave positive signals 121,000–330,000 counts.

The results demonstrate the surprising superiority of the assay where the first primer is immobilized to a solid planar support (Examples 2 and 3), as compared with primer immobilized to beads (Example 1).

Modification and variations of the method and assay of the present invention will be obvious to those skilled in the art from the foregoing detailed description. Such modifications and variations are intended to come within the scope of she following claims.

We claim:

1. A method for detecting a target nucleic acid sequence by a single-stage amplification process conduct ed within a single container, said method comprising:
   (a) conducting, within a single container, an amplification process having only a single stage comprising the following steps:
      (i) providing a first primer hybridizing to the target nucleic acid sequence, wherein the first primer is immobilized on an immobile solid phase support by a direct chemical linkage between the first primer and the solid phase support, wherein the solid phase support forms a part of or is insertable into a container for a sample to be tested,
      (ii) providing a second primer hybridizing to the target nucleic acid sequence in the opposite direction, wherein the second primer is labeled with a detectable label,
      (iii) adding an aliquot of the first primer or other primer(s) to a sample solution containing nucleic acid sequences, in the container together with said first primer of step (i) and said second primer, and
      (iv) reacting the first, second and other primer(s) with the sample containing nucleic acid sequences under conditions which allow amplification of the nucleic acid sequences that hybridize to the first, second and other primers in the container for the sample, and
   (b) within the same container, detecting the presence of bound second primer.

2. The method of claim 1 wherein the container is a microtiter plate well.

3. The method of claim 1 wherein the first primer is immobilized on a solid phase support which is immersible into the container.

4. The method of claim 1 wherein the nucleic acid sequence is amplified by the polymerase chain reaction.

5. The method of claim 1 wherein the nucleic acid sequence is amplified by the nucleic acid sequence based amplification.

6. The method of claim 1 wherein the nucleic acid sequence is amplified by the ligase chain reaction based amplification.

7. The method of claim 1 wherein the nucleic acid sequence is amplified by the Qβ replicase based amplification.

8. The method of claim 1 wherein the nucleic acid sequence is amplified by the strand displacement amplification.

9. The method of claim 1, wherein the nucleic acid sequence is selected from the group consisting of nucleic acid sequences specific to species of organisms, nucleic acid sequences characteristic of a genetic disorder or disease, nucleic acid sequences characteristic of HLA types, nucleic acid sequences which serve to identify an organism, and nucleic acid sequences characteristic of the sex of an organism.

10. The method of claim 1 wherein the label is selected from the group consisting of fluorescent labels, biotin, radiolabels, enzymes specific for chromogenic substrates and dyes.

11. An assay system or kit for detecting a target nucleic acid sequence by a method according to claim 1, said assay system or kit comprising:
   a single container for a sample to be tested,
   a first primer hybridizing to the target nucleic acid sequence, wherein the first primer is immobilized on an immobile solid phase support by a direct chemical linkage between the primer and the solid phase support, wherein the solid phase support forms a part of or is insertable into said container for the sample to be tested,
   a second primer hybridizing to the target nucleic acid sequence in the opposite direction,
   wherein the second primer is labelled with a detectable molecule,
   an aliquot of the first primer, unattached to the immobile solid phase support, and
   reagents for amplification of the sample containing nucleic acid sequences under conditions which allow amplification of the nucleic acid sequences that hybridize to the first and second primers in the container for the sample, wherein said aliquot modifies the amplification of said target sequence by enabling solid phase and solution phase amplification to take place concurrently, and
   reagents for detection of the label on the bound second primer.

12. The assay system or kit of claim 11 wherein the container is a microtiter plate well, further comprising the well plate.

13. The assay system or kit of claim 11 wherein the first primer is immobilized on an immobile solid phase support which is immersible into the container.

14. The assay system or kit of claim 11 wherein the reagents for amplifying the nucleic acid sequence are those for use in the polymerase chain reaction.

15. The assay system or kit of claim 11 wherein the reagents for amplifying the nucleic acid sequence are those for use in the nucleic acid sequence based amplification.

16. The assay system or kit of claim 11 wherein the reagents for amplifying the nucleic acid sequence are those for use in the ligase chain reaction based amplification.

17. The assay system or kit of claim 11 wherein the reagents for amplifying the nucleic acid sequence are those for use in the Qβ replicase based amplification.

18. The assay system or kit of claim 11 wherein the reagents for amplifying the nucleic acid sequence are those for use in the strand displacement amplification process.

19. The assay system or kit of claim 11, wherein the nucleic acid sequence is selected from the group consisting of nucleic acid sequences specific to species of organisms, nucleic acid sequences characteristic of a genetic disorder or disease, nucleic acid sequences characteristic of HLA types, nucleic acid sequences which serve to identify an organism, and nucleic acid sequences characteristic of the sex of an organism.

20. A method for detecting a target nucleic acid sequence by a single-stage amplification process conducted within a single container, said method comprising:

(a) conducting, within a single container, an amplification process having only a single stage comprising the following steps:
  (i) providing a first primer hybridizing to the target nucleic acid sequence, wherein the first primer is immobilized on an immobile solid phase support by a direct chemical linkage between the first primer and the solid phase support, wherein the solid phase support forms a part of or is insertable into a container for a sample to be tested,
  (ii) providing a second primer hybridizing to the target nucleic acid sequence in the opposite direction,
  (iii) adding an aliquot of the first primer or other primer(s) to a sample solution containing nucleic acid sequences, in the container together with said first primer of step (i) and said second primer, and
  (iv) reacting the first, second and other primers with the sample containing nucleic acid sequences under conditions which allow amplification of the nucleic acid sequences that hybridize to the first, second and other primers in the container for the sample and, during the amplification process, labelling the second primer by attaching or incorporating a detectable label, and (b) within the same container, detecting the presence of bound second primer.

21. A method for detecting a target nucleic acid sequence by a single-stage amplification process conducted within a single container, said method comprising:

(a) conducting, within a single container, an amplification process having only a single stage comprising the following steps:
  (i) providing a first primer hybridizing to the target nucleic acid sequence, wherein the first primer is immobilized on an immobile solid phase support by a direct chemical linkage between the first primer and the solid phase support, wherein the solid phase support forms a part of or is insertable into a container for a sample to be tested,
  (ii) providing a second primer hybridizing to the target nucleic acid sequence in the opposite direction,
  (iii) adding an aliquot of the first primer or other primer(s) to a sample solution containing nucleic acid sequences, in the container together with said first primer of step (i) and said second primer, and
  (iv) reacting the first, second and other primers with the sample containing nucleic acid sequences under conditions which allow amplification of the nucleic acid sequences that hybridize to the first, second and other primers in the container for the sample, and (b) within the same container,
  (i) after the amplification process, labelling the second primer by attaching or incorporating a detectable label, and
  (ii) detecting the presence of bound second primer.

22. An assay system or kit for detecting a target nucleic acid sequence by a method according to claim 1, said assay system or kit comprising:

a single container for a sample to be tested, a first primer hybridizing to the target nucleic acid sequence, wherein the first primer is immobilized on an immobile solid phase support by a direct chemical linkage between the primer and the solid phase support, wherein the solid phase support forms a part of or is insertable into said container for the sample to be tested, a second primer hybridizing to the target nucleic acid sequence in the opposite direction, wherein the second primer is labelled with a detectable molecule, amplification means for modifying solid phase amplification which comprises an aliquot of the first primer, unattached to the immobile solid phase support, and reagents for amplification of the sample containing nucleic acid sequences under conditions which allow amplification of the nucleic acid sequences that hybridize to the first and second primers in the container for the sample, wherein said amplification means enables solid phase and solution phase amplification to take place concurrently, and reagents for detection of the label on the bound second primer.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 24 bases
      (B) TYPE: nucleic acid
      (C) STRANDEDNESS: single
      (D) TOPOLOGY: linear    (xi) SEQUENCE DESCRIPTION: SEQ ID NO: 1:

GTT GGC ATG CTT TGA TGA CGC TTC      24

(2) INFORMATION FOR SEQ ID NO: 2:

(i) SEQUENCE CHARACTERISTICS:
      (A) LENGTH: 26 bases
      (B) TYPE: nucleic acid
      (C) STRANDEDNESS: single
      (D) TOPOLOGY: linear    (xi) SEQUENCE DESCRIPTION: SEQ ID NO: 2:

GGC ACC ATT AAA GAA AAT ATC ATT GG      26

(2) INFORMATION FOR SEQ ID NO: 3:

(i) SEQUENCE CHARACTERISTICS:
      (A) LENGTH: 41 bases
      (B) TYPE: nucleic acid
      (C) STRANDEDNESS: single
      (D) TOPOLOGY: linear    (xi) SEQUENCE DESCRIPTION: SEQ ID NO: 3:

TTT TTT TTT GGA TCC GGC ACC ATT AAA GAA AAT ATC ATC TT      41

(2) INFORMATION FOR SEQ ID NO: 4:

(i) SEQUENCE CHARACTERISTICS:
      (A) LENGTH: 15 bases
      (B) TYPE: nucleic acid
      (C) STRANDEDNESS: single
      (D) TOPOLOGY: linear    (xi) SEQUENCE DESCRIPTION: SEQ ID NO: 4:

TCA AAA CAA CGA CAC      15

```
(2) INFORMATION FOR SEQ ID NO: 5:

(i) SEQUENCE CHARACTERISTICS:
        (A) LENGTH:  15 bases
        (B) TYPE:  nucleic acid
        (C) STRANDEDNESS:  single
        (D) TOPOLOGY:  linear (xi) SEQUENCE DESCRIPTION: SEQ ID NO: 5:

TTT CAG AAA GTC GAC                                                    15
```